United States Patent [19]

Gordon

[11] Patent Number: 5,095,104
[45] Date of Patent: Mar. 10, 1992

[54] ANIONIC GLUCOFURANOSE DERIVATIVES, METHODS OF MAKING AND USING THE SAME

[76] Inventor: Paul Gordon, 1220 E. 48th St., Chicago, Ill. 60615

[21] Appl. No.: 563,103

[22] Filed: Aug. 3, 1990

[51] Int. Cl.$^5$ .................. C07G 3/00; C07H 13/02; C07H 15/04; C07H 23/00
[52] U.S. Cl. .................................. 536/4.1; 536/117; 536/118; 536/119; 536/120; 536/121; 536/122
[58] Field of Search .............. 536/4.1, 117, 118, 119, 536/120, 121, 122

[56] References Cited

U.S. PATENT DOCUMENTS

| | | | |
|---|---|---|---|
| Re. 33,000 | 7/1989 | Gordon | 514/25 |
| 3,842,003 | 10/1974 | Netrli | 210/43 |
| 3,862,121 | 1/1975 | Jaques et al. | 536/115 |
| 4,017,608 | 4/1977 | Gordon | 536/120 |
| 4,056,322 | 11/1977 | Gordon et al. | 536/120 |
| 4,251,520 | 2/1981 | Bruzzese et al. | 536/120 |
| 4,735,934 | 4/1988 | Gordon | 514/25 |
| 4,738,953 | 4/1988 | Gordon | 514/25 |
| 4,835,264 | 5/1989 | Liav et al. | 536/4.1 |

OTHER PUBLICATIONS

Takiura et al., Chem. Pharm. Bull., 18:429–435 (1970).
Jorgensen, Vatten, 26(1):2–9 (1970).
Jorgensen, Vatten, 26(2):110–112 (1970).
Jorgensen et al., Vatten, 26(4):350–357 (1970).
Jorgensen, Vatten, 27(1):58–72 (1971).
Jorgensen, Vatten, 29(1):40–51 (1973).
Willenborg et al., FASEB J., 3:1968–1971 (1989).
Tonseth et al., Effluent Water Treatment J., 124–128 (Mar. 1968).
Takiura et al., Chem. Pharm. Bull., 18(10):2125–2177 (1970).

Primary Examiner—Johnnie R. Brown
Assistant Examiner—Everett White
Attorney, Agent, or Firm—Dressler, Goldsmith, Shore, Sutker & Milnamow, Ltd.

[57] ABSTRACT

A glucofuranose derivative substituted at the 3,5,6- or 3,6-positions with a radical that provides an anionic charge at physiological pH values is disclosed, as are pharmaceutical compositions, and methods of making and using the same. The compounds are useful in treating inflammation, and particularly conditions that involve neutrophil influx; they are also useful in inhibiting peptic ulcer formation.

25 Claims, No Drawings

ANIONIC GLUCOFURANOSE DERIVATIVES, METHODS OF MAKING AND USING THE SAME

DESCRIPTION

1. Technical Field

The present invention relates to glucofuranose derivatives, and particularly to glucofuranose derivatives substituted at the 3,5,6- or 3,6-positions with radicals that provide an anionic charge at physiological pH values, as well as to methods of making and using the same.

2. Background Art

Tissue injury can occur or be augmented when endogenous, cellular protective responses are 1) overwhelmed by endogenous or exogenous environmental factors, as loss of oxygen, or an extreme elevation of temperature, or when those protective responses are 2) suppressed, as by stress. Resulting tissue lesions can be a myocardial infarction, a burn, a stomach or duodenal ulcer, or, with the participation of immune and autoimmune response, can include lesions as diverse as allergic hives and rheumatoid arthritis. Also, the initial tissue injury, minor, trivial or otherwise, if begun by antihomoeostatic factors, can be prolonged and complicated by the inflammation that it initiates.

The mammalian inflammatory response is a very complicated process, which, however always includes salient characteristics that can augment tissue injury. These include degrees of loss of microvessel integrity, in which there occurs 1) assaultative fenestration of the microvasculature, with accompanying leakage of the fluid elements of the blood into interstitial spaces, and 2) chemotactically directed migration of blood leukocytes into the inflamed tissues.

Inflammation can occur when the mammal's tissues are injured as by a bone break or sprain, ulceration or during reperfusion after an ischemic attack. In these instances, the inflammation is a response to one or more "self" molecules of the injured mammal. Inflammation can also occur by invasion of the mammalian tissues by "non-self" materials such as bacteria and dust particles in the lungs.

During an inflammatory response, chemical mediators such as histamine, 5-hydroxytryptamine, chemotactic factors, bradykinin, leukotrienes and prostaglandins are liberated locally. Phagocytic cells migrate to the area and cellular lysosomal membranes may be ruptured, releasing lytic enzymes.

On a macroscopic level, inflammation is accompanied by clinical signs such as erythema, swelling, pain and warmth.

Migration of leukocytes into an inflamed area is an important aspect of the inflammatory process. Of the leukocytes, T cells and phagocytic cells play a key role.

Of the phagocytic cells that migrate to a site of inflammation, neutrophils are among the most prominent in that those cells constitute about 45 to about 70 percent of all the leukocytes in an adult human. In addition, neutrophils not only phagocytose invading "non-self" substances, such as bacteria, but also secrete powerful redox agents, such as the superoxide anion radical, and secrete, as well, proteases and other lytic enzymes.

Phagocytic cells of the circulation are particularly drawn to sites of injury or bacterial infection by chemotactic factors that are generated from blood complement proteins or that are released by the injured cells or bacteria. Chemotaxis of phagocytic cells to the site of a bacterial infection is a desirable event in ridding the body of the invading microorganism.

However, chemotaxis and the resulting influx of phagocytic cells such as neutrophils to a site of injury can actually add to the injury due to the phagocytosis and secretions provided by the neutrophils. For example, Chan et al., *Neurobiology*, 34:315-320 (1984) reported on the damage caused to brain cells by the superoxide radical anion, hydrogen peroxide and hydroxyl radicals, and postulated that those oxygen-derived free radicals secreted by neutrophils play a role in cerebral ischemia and trauma. Similarly, the complement fragment C5a is a prime inducer of unwanted inflammation in diverse human disease conditions as in patients having had heart attacks that are treated with clot-lysing agents and enter the reperfusion period [Lucchesi, *Ann. Rev. Physiol.* 52:561-576 (1990)] and in allergic states [Muller-Eberhard, Chapter 4, in *Textbook of Immunopathology*, Vol. 1, Miescher et al. eds., Grune & Stratton, New York (1968)]. C5a is a potent chemotactic agent for neutrophils.

It would therefore be beneficial if both loss of microvessel integrity and chemotaxis and neutrophil influx to a site of injury and incipient or established inflammation could be reduced or otherwise controlled.

BRIEF SUMMARY OF THE INVENTION

The present invention contemplates a compound that is a glucofuranose derivative substituted at the 3,5,6- or the 3,6-positions with a radical that provides an anionic charge at physiological pH values. Such a compound has the structural formula

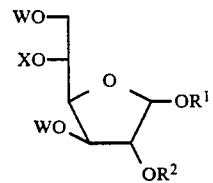

wherein W is selected from the group consisting of $SO_3M$, $PO_3M_2$ and $R^5CO_2M$ in which $R^5$ is $(CH_2)_n$, where n is 1-5;

X is H or W;

$R^1$ and $R^2$ are independently H or $C_1$-$C_6$ alkyl, with the total number of carbon atoms in $R^1$ plus $R^2$ being 9 or fewer; or $R^1$ and $R^2$ together form a $CR^3R^4$ group in which (a) $R^3$ and $R^4$ are independently selected from H or $C_1$-$C_6$ alkyl with the total number of carbon atoms in $CR^3R^4$ being 9 or fewer, or (b) $CR^3R^4$ together from an unsubstituted cycloaliphatic group containing a total of 5-9 carbon atoms in the ring; and M is selected from the group consisting of a proton, an alkali metal ion, an alkaline earth metal ion and an ammonium ion.

It is preferred that W be a before-defined $S_3M$ group where the substitution is at the 3,5,6-positions and $PO_3M_3$ when substitution is at the 3,6-positions. It is also preferred that $R^1$ and $R^2$ together form a $CR^3R^4$ group in which $R^3$ and $R^4$ are the same alkyl group or hydrogen. More preferred of those same $R^3$ and $R^4$ groups are hydrogen and $C_1$-$C_3$ alkyl, and most preferably, $R^3$ and $R^4$ groups are both $C_1$-$C_2$ alkyl groups. Thus, where $R^1$ and $R^2$ together form a symmetric $CR^3R^4$ group (an alkylidene group) there are preferably a total of 1 to 7 carbon atoms in the symmetric alkylidene group, and most preferably there are a total of 3 or 5 carbon atoms in the symmetric alkylidene group.

A -pharmaceutical composition containing a before-defined compound as active agent is also contemplated. That pharmaceutical composition contains an anti-inflammatory or anti-ulcer effective amount of active agent dissolved or dispersed in a -physiologically tolerable diluent. A pharmaceutical composition can be in solid or liquid form suitable for administration orally or parenterally.

A method of treating an inflammatory condition in a mammal is also contemplated. Here, an anti-inflammatory or anti-ulcer amount of a before-described compound, typically present in a before-described pharmaceutical composition is administered to a mammal. Single and multiple administrations are contemplated.

The present invention has several benefits and advantages.

One benefit is that use of its method lessens swelling (edema) associated with inflammation.

Another benefit is that use of its method inhibits influx of neutrophils to a site of injury or other inflammation.

Yet another benefit of this invention is that its use inhibits gastric ulcer formation that can accompany use of indomethacin, and related NSAIDs.

An advantage of the invention is that the compounds are relatively non-toxic.

Another advantage of the invention is that the compounds are readily prepared from commercially available precursors.

Still further benefits and advantages will be apparent to a worker skilled in the art from the disclosure that follows.

DETAILED DESCRIPTION OF THE INVENTION

I. The Compounds

A. Anionic Sugars of the Art

The compounds of the present invention are glucofuranose derivatives substituted with a radical that provides an anionic charge at physiological pH values. These compounds are discussed in detail hereinafter.

The principal pharmacologically active sulfated sugars are polymers and include materials such as heparins, heparans and sulfates of dextran. Research results have indicated that the above polymers lose pharmacological activity as the polymer length decreases toward sulfated monomers. It was therefore unexpected that the compounds of the invention had pharmacological activity, and surprising that they are as potent as they are found to be. It is still further surprising that a compound of the invention lacks the anti-coagulant activity that is so characteristic of the above polymers; that activity in the case of dextran sulfate having been shown to be an undesirable side effect when anti-viral activity was sought.

A particularly useful group of new compounds of the invention are salts of 3,5,6-tri-O-sulfo-D-glucofuranose and its 1- and 2-ether derivatives. Different, known sulfated sugars, and particularly D-glucopyranose-1,3,6-trisulfate, as well as the trisulfates of D-mannose, D-galactose, and D-fructose are reported by Takiura et al., *Chem. Pharm. Bull.*, 18:429-435 (1970). A material referred to as glucose trisulfate also referred to as starch sulfate was also reported as useful in precipitating proteins from slaughterhouse wastes in a series of papers by Jorgensen [*Vatten*, 25(3):278-288 (1969); *Vatten*, 26(1):2-8 (1970); *Vatten*, 26(2):110-112 (1970); *Vatten*, 26(4):350-357 (1970); *Vatten*, 27(1):58-72 (1971); and *Vatten*, 29(1):40-51(1973)]. Sulfated sucrose, lactose and starch are also reported as useful in waste precipitation in U.S. Pat. No. 3,842,003.

Mannose-6-diphosphate is known to be useful in treating inflammation experimental allergic encephalomyelitis (EAE), a cell-mediated autoimmune demyelinating disease of the central nervous system. Mannose-1,6-diphosphate and fructose-1,6-diphosphate, the only polyphosphate sugar esters studied, were reported to be less effective than mannose-6-phosphate in inhibiting the inflammation. [Willenborg et al., *FASEB J.*, 3:1968-1971 (1989).]

B. Compounds of the Invention

A compound of the present invention is a glucofuranose substituted at the 3,5,6- or 3,6-positions by a radical that provides an anionic charge (is anionic) at physiological pH values, e.g., pH 7.2-7.4. The anionic charge of that radical is neutralized in a compound by a pharmacologically acceptable counter ion M, that is preferably monovalent such as a proton, an alkali metal ion such as sodium or potassium, or an ammonium ion such as $NH_4^+$ itself or a pharmacologically (pharmaceutically) acceptable alkyl- or saccharoammonium ion such as protonated diethylaminoethanol or glucosamine. Divalent alkaline earth metal salts such as calcium and magnesium ions are also contemplated.

The remaining available hydroxyl groups of the glucofuranose ring; i.e., the 1-, 2- and sometimes 5-hydroxyl (when unsubstituted by an anionic radical) can be unsubstituted (free hydroxyl groups), or, more preferably, the 1- and 2-hydroxyl groups are etherified. When the 1- and 2-position hydroxyl groups are etherified, the non-glucofuranose portion of the ether groups is saturated, and can contain a total of 9 carbon atoms. The non-glucofuranose portion of an ether group is an alkyl or alkylidene group.

An alkyl portion of the ether group can be exemplified by a $C_1-C_6$ alkyl group such as methyl, ethyl, isopropyl, sec-butyl, pentyl, hexyl, cyclopentyl or cyclohexyl. For ease in synthesis, it is preferred that both alkyl groups be the same.

An alkylidene ether is a ketal or an acetal. Symmetrical ketals prepared from unsubstituted cyclic ketones having 5-9 carbon atoms in the ring or ketones having an odd number of carbon atoms in a chain with the keto group at the central carbon (symmetric ketones) are preferred because of their relative ease of manufacture, since only one isomer is possible as compared with a ketal prepared from an unsymmetrical ketone or an acetal formed from an aldehyde other than formaldehyde. Exemplary alkylidene groups include methylene, 2-propylidene, 3-pentylidene, 4-heptylidene and 5-nonylidene, as well as cyclopentylidene, cyclohexylidene, cycloheptylidene, cyclopentylidene and cyclononylidene. An alkylidene group containing 1 to 7 carbon atoms is preferred, whereas an alkylidene group containing 3-5 carbon atoms is more preferred.

A substituted glucofuranose having a 1,2-ketal formed from acetone; i.e., a 2-propylidene (isopropylidene) group, is particularly preferred.

The radical that provides anionic charge at physiological pH values can be a sulfo (sulfate) radical, a phosphono (phosphate) radical or a carboxyl (carboxylate)

radical. Sulfo (sulfate) radicals are particularly preferred. When a carboxyl radical is present, that radical is separated from the glucofuranose oxygen atom by one to five methylene ($CH_2$) groups.

Each compound useful herein is a glucofuranose. Both the D- and L-series of glucofuranose compounds are contemplated, although the D- series is particularly preferred.

A compound of the invention can be represented as having the structural formula shown below as I.

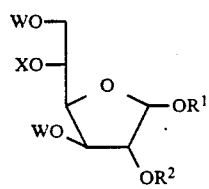

I wherein W is selected from the group consisting of $SO_3M$, $PO_3M_2$ and $R^5CO_2M$ in which $R^5$ is $(CH_2)_n$, where n is 1-5;

X is H or W;

$R^1$ and $R^2$ are independently H or $C_1$-$C_6$ alkyl, with the total number of carbon atoms in $R^1$ plus $R^2$ being 9 or fewer; or $R^1$ and $R^2$ together form a $CR^3R^4$ group in which (a) and $R^3$ and $R^4$ are independently selected from H or $C_1$-$C_6$ alkyl with the total number of carbon atoms in $CR^3R^4$ being 9 or fewer, or (b) $CR^3R^4$ together from an unsubstituted cycloaliphatic group containing a total of 5-9 carbon atoms in the ring; and M is selected from the group consisting of a proton, an alkali metal ion, an alkaline earth metal ion and an ammonium ion.

W is $SO_3M$ and X is W ($SO_3M$) in a most preferred compound of the above formula. It is also most preferred that $R^1$ and $R^2$ form a $CR^2R^3$ group. In a particularly preferred compound, W is $PO_3M_2$ and X is H.

Exemplary compounds of the invention, including most preferred and particularly preferred compounds of the D- series, are illustrated below, in which M is as discussed before, and are identified by Roman numerals. The names for those compounds are listed beneath the structures, adjacent to corresponding Roman numerals, using the potassium salts as exemplary.

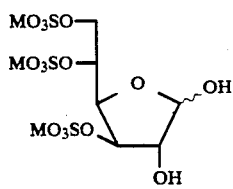

II

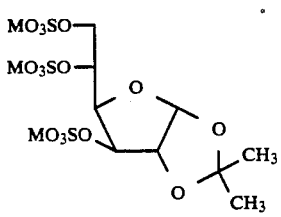

III

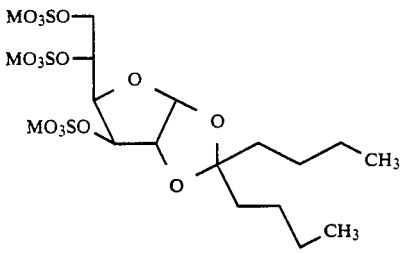

IV

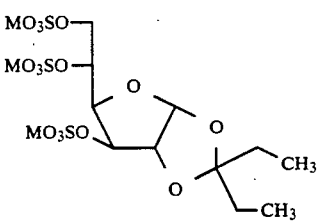

V

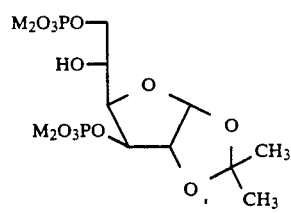

VI

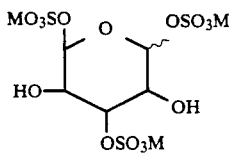

VII

II. 3, 5, 6-Tri-O-sulfo-α-D-glucofuranose, tripotassium salt.

III. 1,2-O-(2-Propylidene)-3, 5, 6-tri-O-sulfo-α-D-glucofuranose, tripotassium salt.

IV. 1, 2-O-(5-Nonylidene)-3, 5, 6-tri-O-sulfo-α-glucofuranose, tripotassium salt.

V. 1, 2-O-(3-Pentylidene)-3, 5, 6-tri-O-sulfo-α-D-glucofuranose, tripotassium salt.

VI. 1, 2-O-(2-Propylidene)-3, 6-di-O-phospho-α-D-glucofuranose, tetrapotassium salt.

VII. 1, 3, 6-Tri-O-sulfo-α-D-glucopyranose, tripotassium salt, a compound of the prior art utilized for purposes of comparison. This compound was prepared by the procedure of Takiura et al., Chem. Pharm. Bull., 18: 429-435 (1970).

The wavy line joining the 1-position hydroxyl group to the ring in Compound II indicates that the stereochemistry can be either α or β, since that hydroxyl group is bonded to the anomeric carbon atom. Following usual custom, ring-bonded hydrogen atoms are not illustrated for ease in understanding.

II. Compositions and Methods

A before-described compound has -pharmaceutical properties in treating inflammatory or ulcerative and related conditions, as is discussed hereinafter. When used to treat inflammation, an anti-inflammatory amount of a compound is dissolved or dispersed in a physiologically tolerable (pharmaceutically acceptable) diluent to form a pharmaceutical composition.

A compound of the invention is effective when administered orally and also when administered parenterally. Oral administration is the preferred mode of administration.

Liquid compositions and tablets or other dosage forms are preferably themselves buffered to provide a physiological pH value when administered or upon dissolution. For preparations designed to dissolve in the stomach, provision of -physiological pH values is of less import since the stomach and gastrointestinal tract provide their own pK values and buffering systems.

When the compound is to be administered orally, it can be admixed with a filler and/or binder such as starch and a disintegrator, and the admixture can be pressed into a tablet of a size convenient for administration orally. The solid, particulate compound can also be placed into a capsule. Alternatively, a water solution or suspension of a salt complex, or an admixture thereof with a flavored syrup such as cherry syrup, can be administered orally.

When a compound is administered parenterally as by injection or intravenously, it is usually dissolved in a physiological saline solution that contains sodium chloride in sufficient concentration to make the overall solution to be injected isotonic to body fluids. In treating some patients or when convenient, a compound in aqueous solution can also be administered by nasopharyngeal spray. Administration also can be by means of a suppository in patients unable to retain medication administered by mouth. Suitable pharmaceutically acceptable carriers and techniques in addition to those mentioned above, as are well known, can be used when desired.

The dosage can be varied over extremely wide limits, as a compound is effective at low dosage levels and is relatively nontoxic and free of adverse side effects. A compound can be administered in the minimum quantity which is effective; i.e., in an amount sufficient to reduce or inhibit inflammation or ulcer formation. The dosage can be increased as desired up to the maximum effective dosage tolerated by the patient.

A compound is usually administered in an amount of about 0.2 to about 150 milligrams, or preferably at about 1 to about 50 milligrams, per kilogram of body weight per day, and more preferably in an amount of about 10 to about 50 milligrams per kilogram of body weight per day, over the period required for treatment.

A compound of the invention is utilized in a method of treating an inflammatory or ulcerative condition in a mammal such as a laboratory animal, like a mouse, rat or rabbit, a veterinary animal like a dog, horse or cow, or a primate such as a human or ape. In accordance with this method, a compound of the invention is administered to a mammal in need thereof in an anti-inflammatory or anti-ulcer amount. The compound is maintained within the treated mammal until the compound is excreted or metabolized by usual bodily means.

The compound is administered in a previously discussed pharmaceutical composition. A single dose administration can be utilized, but in general practice, multiple doses over a several day time period are used, with the treatment continuing until the inflammation ceases.

A method of the present invention is useful in treating inflammation generally, as well as specifically where neutrophils are or may be implicated. For example, a compound of the invention can be used to lessen the edema associated with an inflammatory condition. Edema can be caused by a complement component such as fraction C5a as induced by zymosan, as well as by non-complement-related inflammatory agents such as trypsin, collagenase and carrageenan. A compound of the invention is shown hereinafter to be useful in reducing the edema caused by C5a (zymosan), trypsin, bacterial collagenase and carrageenan.

In addition, a compound of the invention acts to inhibit neutrophil chemotaxis, thereby inhibiting influx of neutrophils to a site of injury or other inflammation. For example, clot-lysing enzymes such as t-PA, urokinase and streptokinase as are utilized in treatment of heart attacks can lead to ischemic inflammation once the blood starts flowing after a clot is lysed. Compounds of the invention are shown hereinafter to be useful in reducing swelling during post-ischemic reperfusion.

The drug allopurinol is often utilized to suppress experimental reperfusion injury. That drug is utilized near its toxic level at about 20–30 milligrams (mg)/kilogram (kg). A compound of the present invention can achieve a similar result to that achieved by allopurinol, but at a much lower dose; i.e., 0.1–0.2 mg/kg. The dose of one compound used to achieve that result in rats was about 1/1000 the $LD_{50}$ value for mice.

In vitro studies show that compounds of this invention are more active in inhibiting neutrophils chemotaxis than the anion channel blockers probenecid and SITS (4-acetamido-4'-isothiocyano-stilbene-2,2'-disulfonate), and are more effective than are ibuprofen and prednisone. Prostaglandin $E_2$ ($PGE_2$) was about equally as active as Compound III, and Compound III was more active than any of the other assayed compounds. These results parallel assays for neutrophils present in vivo in inflamed tissues.

A compound of this invention can also be used to treat gastric ulceration. Here, gastric ulcers were induced in laboratory rats by a combination of stress caused by injection of zymosan and zymosan-activated serum into rat paws, and the administration of indomethacin. Ulcer reduction using the same stimulus and either 17.5 mg/kg of Compound III or 25 mg/kg cimetidine was greater using Compound III than cimetidine.

A compound of the present invention was also shown to be useful in inhibiting gastric ulceration in rats, induced by ethanol, ethanol plus heparin, and stress plus ethanol plus heparin, and paw-injected zymosan plus stress. Here, ethanol alone produced ulcers in rat stomachs, and the number of ulcers produced was reduced by administration of a compound of the invention. Administration of ethanol plus heparin induces production of ulcers 24 hours later, many of which bleed. Treatment with a compound of the invention again reduced the number of ulcers produced, and no bleeding ulcers were observed.

III. Compound Synthesis

A compound of the present invention can be readily prepared from commercially available precursors. Several useful precursors are available from Pfanstiehl Laboratories, Inc.

The 3,5,6-tri-sulfate derivatives are particularly preferred compounds of the invention. A typical synthesis is discussed below using 1,2-O-(isopropylidene)-3,5,6-D-glucofuranose trisulfate, Compound III, as exemplary.

1,2-O-Isopropylidene-α-D-glucofuranose (Compound A) is commercially available from Pfanstiehl, and can also be prepared from commercially available 1,2,5,6-diisopropylidene-D-glucose (diacetone-D-glucose) by mild acid hydrolysis. Compound A is dissolved in anhydrous pyridine with vigorous stirring, and the resulting solution is cooled to about $-30°$ C. in a dry ice/acetone bath.

Excess chlorosulfonic acid in an inert solvent such as chloroform, tetrahydrofuran (THF) or methylene chloride is admixed portion-wise with the pyridine solution, while maintaining the temperature of the resulting reaction mixture between about $-30°$ C. and $-15°$ C. The reaction mixture is permitted to warm to room temperature after all of the chlorosulfonic acid has been added and the resulting exotherm has subsided.

Aliquots are thereafter taken and assayed for completeness of reaction using electrophoresis. After the reaction is complete, the reaction mixture is again cooled in a dry ice/acetone bath to a temperature below about $-15°$ C., and a mixture of water and pyridine (about 1:4, v/v) is added to decompose the excess chlorosulfuric acid.

In one procedure, barium hydroxide is added to a pH value up to about 7.0 to precipitate the sulfate ion generated by the excess chlorosulfonic acid. After removal of the precipitate, solid carbon dioxide (dry ice) is added to remove most of the barium ions present. The resulting precipitate is filtered and the filtrate is concentrated to dryness.

The dried filtrate is dissolved in water and passed through an ion exchange resin, potassium form, to form the tripotassium salt. Replacement of potassium ion by sodium or ammonium ions in the resin and passage of the redissolved filtrate over the column provides the corresponding sodium or ammonium salts. The resulting aqueous eluate is then concentrated in vacuo and purification of the desired compound can be achieved by recrystallization as with methanol/water.

More preferably, the pyridine/water solution obtained after decomposition of the excess chlorosulfonic acid is concentrated in vacuo to provide a viscous oil that is usually brown in color. Addition of an aqueous solution of an appropriate cation hydroxide such as potassium hydroxide to a pH value of about 6.5-7 provides the desired cation without the need for using barium. Concentration of the cation hydroxide solution followed by recrystallization as above provides the desired compound as white crystals.

The corresponding disulfate can be prepared by stopping the above sulfonation prior to completion of the sulfonation reaction and separating out the disulfate as by preparative electrophoresis. The disulfate is more preferably prepared by use of only two moles of chlorosulfonic acid per mole of Compound A.

Compounds having hydroxyl groups at the 1- and 2-positions ($R^1$ and $R^2$ are H in Formula I, Compound II), as well as those compounds having different groups bonded to the oxygens of the 1- and 2-positions are typically prepared from the above-prepared trisulfate. For example, Compound II, before, is prepared by acid hydrolysis of Compound III, followed by neutralization with an appropriate cation hydroxide such as potassium hydroxide.

The hydroxyl groups of the 1- and 2-positions of Compound II can thereafter be reacted as desired to provide the other than hydrogen $R^1$ and $R^2$ groups of a compound of Formula I. It is often more convenient, particularly where $R^1$ and $R^2$ together form an alkylidene group, to link the $R^1$ and $R^2$ substituents prior to adding the anionic radicals.

For example, where $R^1$ and $R^2$ together form a 3-pentylidene group, D-glucose is reacted with excess 3-pentanone in the presence of zinc chloride and an acid to form the 1,2:5,6-di-O-(3-pentylidene)-α-D-glucofuranose derivative. That compound can then be partially deblocked with mild acid to form the 1,2-O-(3-pentylidene) derivative that is reacted with a source of the anionic radical, e.g., chlorosulfonic acid, neutralized with an appropriate cation hydroxide and then crystallized as discussed before.

1,2-$C_5$-$C_9$ Cyclic alkylidene derivatives are also preferably prepared by formation of the 1,2:5,6-di-O-cyclic alkylidene-glucofuranose route in a manner analogous to that discussed immediately above.

In another procedure that is particularly useful for preparation of the 1,2-O-(5-nonylidene)glucofuranose derivatives, D-glucurono-6,3-lactone is utilized as the starting material. The 1,2-O-(5-nonylidene) group is added as discussed before for other ketones. The resulting 1,2-O-(5-nonylidene)-D-glucurono-6,3-lactone is then reduced with borane in THF or another solvent to provide the corresponding glucofuranose derivative that is thereafter reacted with an appropriate source of the anionic radical to form the desired compound.

A compound of the invention wherein $R^1$ and $R^2$ are $C_1$-$C_6$ alkyl is typically prepared by first preparing an appropriate 1- and 2-substituted glucopyranose, which is thereafter converted to a corresponding glucofuranose, and then to a 3,5,6-trisubstituted or 3,6-disubstituted derivative, as desired. An exemplary synthesis for a 1,2-dialkoxy-glucofuranose is discussed below.

3,4,6-Tri-O-benzyl-D-glucal is prepared from commercially available 3,4,6-tri-O-acetyl-D-glucal (Aldrich Chemical Co.) using the method of Blackburne et al., *Aust. J. Chem.*, 29:381 (1976) The 3,4,6-tri-O-benzyl-D-glucal is coupled with an alcohol whose alkyl portion is the $R^1$ $C_1$-$C_6$ alkyl group using the method described in Friesen et al., *J. Am. Chem. Soc.*, 111:6656 (1989), which coupling forms a corresponding 1-α-$C_1$-$C_6$ alkoxy-2-β-iodo-glycoside. Briefly, the glycal and an excess of the alcohol are stirred in methylene chloride in the presence of molecular sieves to which solid I(sym-collidine)$_2$-ClO$_4$ is added to effect haloetherification. [See also, Lemieux et al., *Can. J. Chem.*, 43:2190 (1965), and the citations therein.]

The β-iodo group in the above glycoside is replaced with inversion of configuration by reaction with a metal salt of an alcohol whose alkyl portion is the $R^2$ $C_1$-$C_6$ alkyl group. Thus a 2-O-$C_1$-$C_6$-alkyl-3,4,6-tri-O-benzyl-1-$C_1$-$C_6$-glucoside is formed.

The benzyl groups are thereafter removed by standard procedures, as by hydrogenolysis, to form a 2-O-$C_1$-$C_6$-alkyl-1-$C_1$-$C_6$-glucoside, which is in the glucopyranoside form. The formed glucopyranoside can be converted into the glucofuranoside by using the method described in Yamaguchi et al., *Carbohydrate Research*, 59:129 (1977).

Briefly, a glucopyranoside is stirred in an alcohol solvent in the presence of an acid catalyst such as Amberlite ® CG-120(H+). The alcohol solvent used contains the same $C_1$-$C_6$ alkyl group as is present in the $R^1$ alkyl group. The resulting furanoside is recovered and α- and β-anomers are typically separated. The resulting furanoside is thereafter reacted with an appropriate reagent to form a desired anionic glucofuranose, as is also discussed herein.

Compounds having a phosphate monoester as the anionic group are typically prepared from the corresponding compound whose 1- and 2-position hydroxyl groups are etherified. Here, for example, diphenyl chlorophosphate is the source of the anionic radical. The resulting phosphate triester is hydrogenated over platinum to cleave the phenyl ester groups from phosphorus atom. Neutralization of the phosphoric acid ester with an appropriate cation hydroxide provides the desired compound.

A compound containing a carboxyl anionic group is exemplified by the carboxymethyl derivative. Here, a compound such as Compound A is reacted with hydroxide ion in the presence of a halo-substituted carboxylic acid such as an omega-halo carboxylic acid like chloroacetic acid to effect etherification of the sugar hydroxyl groups. The cation of the hydroxide ion utilized in the reaction is typically the ultimately desired cation so that cation exchange is unnecessary. The produced carboxylate is then recovered by chromatography and/or crystallization.

Best Mode for Carrying Out the Invention

Materials and Methods

Nuclear magnetic resonance (NMR) spectra were recorded by means of a Varian XL-300 spectrometer. Optical rotations were measured on a Perkin Elmer Model 241 polarimeter using a 1 dm microcell. Decomposition points were determined in capillary tubes on a Mel-Temp II melting point apparatus from Laboratory Devices (Holliston, MA).

Thin layer chromatographs (TLC) were developed on 5 cm glass slides coated with 0.25 mm silica gel 60 $F_{254}$ supplied by E. Merck. The solvent system used in TLC studies was n-propanol/ethyl acetate/water/ammonium hydroxide (5:2:2:1). Compounds were visualized by charring with a 10 percent aqueous solution of sulfuric acid.

Paper electrophoresis studies were performed using an EC135 power supply and an EC370 minicell from E-C Apparatus Corporation (St. Petersburg, FL). In each study, a potential of 200 V was applied for 30 minutes on Whatman chromatography paper (3 mm Chr; cat. #3030861) cut to 6 cm ×14 cm. The buffer used was acetic acid-pyridine (pH 6.5), prepared by mixing 0.05 M acetic acid with pyridine. Compounds were detected by spraying the paper with 2 percent aniline hydrogen phthalate reagent and heating to 150° C. for 20 minutes. Migration values (M) were determined relative to a glucose-6-sulfate standard.

Atomic absorption (AA) experiments were performed by Schwarzkopf Microanalytical Laboratory (Woodside, NY). Elemental analyses were carried out by Midwest Microlab (Indianapolis, IN).

EXAMPLE 1

1,2-O-(1-Isopropylidene)-3,5,6-tri-O-Sulfo-D-Glucofuranose, Tripotassium Salt (Compound III)

1,2-O-Isopropylidene-α-D-glucofuranose [100 grams (g); 0.45 moles] was dissolved in anhydrous pyridine [1 liter (1)] with vigorous stirring, and the resulting solution coded to about −30° C. in a dry ice/acetone bath. Chlorosulfonic acid [185 g; 1.59 moles, d=1.753 g/ml] in chloroform (570 ml) was added in portions while maintaining the resulting reaction mixture at a temperature of about −30° C. to about −15° C. The temperature of the reaction mixture was permitted to rise to room temperature over a period of about 15-20 hours.

The progress of sulfonation is monitored by paper electrophoresis and thin layer chromatography (TLC). The TLC solvent used was 5:3:1:1 (v/v) n-propanol:ethyl acetate:water:ammonium hydroxide. Recovery of the reaction product began after all of the disulfate product had been converted to trisulfate.

With the temperature of the reaction mixture again cooled to below about −15° C., water (55 ml) in pyridine (200 ml) was added slowly to the reaction mixture to decompose the excess chlorosulfonic acid. Two recovery processes were used.

Recovery #1

This recovery method is a modification of that described by Whistler et al., *Methods in Carbohydrate Chemistry*, Vol. 2, Academic Press, New York (1963) for the preparation of D-glucose-6-sulfate.

The above reaction mixture was warmed to room temperature and adjusted to pH 7 by the addition of saturated barium hydroxide. About 10 1 of $Ba(OH)_2$ solution was required. A white precipitate of $BaSO_4$ was formed. Care was taken to maintain the pH value at about 7 as higher pH values lead to product degradation and a brown coloration.

The resulting solution was concentrated in vacuo to about 2 1 at 35° C. The solid was removed by filtration. Solid $CO_2$ (dry ice) was added to the filtrate to precipitate $BaCO_3$, which was filtered off, and the filtrate was concentrated in vacuo to dryness.

A Dowex 50X8-200 ion exchange resin, hydrogen form, was prepared. The dried filtrate, above, was dissolved in a minimum amount of water and applied to the column. The acidic eluant was collected and neutralized to a pH value of 7, and then concentrated in vacuo at 35° C.

The resulting product was recrystallized three times from methanol/water. Yield=47 g (18 percent), as a white crystalline solid.

Analytical analysis:

TLC $R_f$=0.3; M (glucose-6-sulfate)=1.6; decomposition point 190° C.; Ba analysis by AA<42 ppm; $[\alpha]_D^{25}$−5.3° (c 0.8, $H_2O$); $^1$H NMR ($D_2O$, chemical shifts relative to TMSPA γ6.10 (d, 1H), 5.09 (d, 1H), 4.90 (d, 1H), 4.89–4.83 (m, 1H), 4.70–4.66 (m, 1H), 4.57–4.52 (m, 1H), 4.26–4.21 (m, 1H), 1.55 (s, 3H), 1.39 (s, 3H). Analysis calculated for $C_9H_{13}K_3O_{15}S_3$: 18.81; H, 2.28; S, 16.74. Found: C, 17.52; H, 2.29; S, 15.39.

Recovery #2

Another sample of the sulfonation reaction product was prepared, treated with water/pyridine as before and warmed to room temperature. The reaction mixture was concentrated in vacuo at 35° C. to form a brown, viscous oil. That oil was then neutralized directly with a 1 molar (M) aqueous KOH solution to a pH value of 6.5-7. That solution was reconcentrated in vacuo at 35° C. to provide an off-while solid. That solid was recrystallized as above to provide high purity, white crystals. Yield=132 g (51 percent).

Analytical analysis:

TLC $R_f$=0.3; M (glucose-6-sulfate) =1.6; decomposition point 190° C.; $[\alpha]_D^{25}$−5.5° (c 2.0, $H_2O$); $^1$H NMR ($D_2O$, chemical shifts relative to TMSPA γ6.10 (d, 1H), 5.09 (d, 1H), 4.90 (d, 1H), 4.89–4.83 (m, 1H), 4.70–4.66 (m, 1H), 4.57–4.52 (m, 1H), 4.26–4.21 (m, 1H), 1.55 (s, 3H), 1.39 (s, 3H). Analysis calculated for $C_9H_{13}K_3O_{15}S_3$: C, 18.81; H, 2.28; S, 16.74. Found: C, 8.43; H, 2.21; S, 15.69.

EXAMPLE 2

3,5,6-Tri-O-Sulfo-α-D-Glucofuranose, Tripotassium Salt (Compound II)

A solution of 1,2-O-(2-isopropylidene)-3,5,6-tri-O-sulfo-α-D-glucofuranose, tripotassium salt (15 g, 26 mmole) (Compound III) in 0.2 M sulfuric acid (500 mL) was stirred and heated at 40° C. for 10 hours. Analysis of the reaction mixture by TLC and paper electrophoresis indicated that hydrolysis was complete.

The reaction mixture was allowed to cool to ambient temperature and was then neutralized to pH 7 by the portionwise addition of a saturated barium hydroxide solution. The formed precipitate was removed by filtration and the solution was concentrated under reduced pressure to one-half of its original volume. Additional precipitate was removed by filtration. Carbon dioxide was then added to the filtrate and the newly formed precipitate was also removed by filtration. The resulting filtrate was concentrated under reduced pressure to leave a yellow, viscous oil.

The product was applied to an ion exchange column which was prepared using Dowex 50X8-200 (H+ form) ion exchange resin. Following elution with water, the fractions containing the desired product were combined and neutralized to pH 7 by adding 1 M potassium hydroxide solution. The solvent was then removed under reduced pressure.

The product was dissolved in the minimum quantity of water and methanol was added gradually. The purified potassium salt of the trisulfate was precipitated as an amorphous powder. This procedure was repeated two additional times to yield 8.9 g (64 percent) of a slightly hygroscopic light beige powder: TLC $R_f$=0.2; M (glucose-6-sulfate) =1.6; decomposition point 190° C.; $^1$H NMR (D$_2$O, chemical shifts relative to TMSPA) γ5.55 (d, 1H), 5.36 (d, 1H), 4.98–4.54 (m, 2H), 4.50–4.08 (m, 3H). Analysis calculated for $C_6H_9K_3O_{15}S_3$: C, 13.48; H, 1.70; S, 17.99. Found: C, 14.14; H, 2.16; S, 14.62.

EXAMPLE 3

1,2:5,6-di-O-(3-pentylidene)-α-D-glucofuranose

To anhydrous dextrose (26.5 g, 147 mmole) in freshly distilled 3-pentanone (285 g, 3.31 moles) was added zinc chloride (31.8 g, 233 mmole) which had been freshly fused and pulverized. With vigorous stirring, phosphoric acid (99 percent) (0.53 g, 5.4 mmole) was added. Stirring was continued and the mixture was heated to 40° C. for 48 hours.

After cooling to ambient temperature, the solids were removed by filtration and rinsed with ethylene dichloride. Solid sodium carbonate was added to the filtrate until a pH of 7.5 was reached. This mixture was again subjected to filtration. The collected solids were diluted with an equal volume of ethylene dichloride and a 20 percent aqueous solution of sodium bicarbonate was added. The solids which were formed were removed by filtration and the organic layer was separated and extracted two additional times with 10 percent sodium bicarbonate solution. The organic extract was washed once with water, dried over anhydrous magnesium sulfate, filtered, and concentrated under reduced pressure to leave a viscous yellow oil.

The crude product was distilled under high vacuum and the desired compound distilled at 150–160° C. (0.20 mm Hg) as a light yellow viscous oil. From the distillation, 9 g (20 percent) of the product was obtained: TLC $R_f$(hexane/ethyl acetate, 3:1) =0.25.

EXAMPLE 4

1,2-O-(3-pentylidene)-α-D-glucofuranose

To a mixture of methanol (75 ml) and 0.8 percent aqueous sulfuric acid (75 ml) was added 1,2:5,6-di-O-(3-pentylidene)-α-D-glucofuranose (14 g, 44 mmole). The solution was stirred at ambient temperature for 20 hours.

The reaction mixture was then neutralized to pH 7 with barium carbonate. The mixture was filtered and the filtrate was concentrated under reduced pressure to leave an off-white solid.

The product was recrystallized twice from ethyl acetate/methanol to afford 6.8 g (63 percent) of a white crystalline solid: TLC $R_f$ (hexane/ethyl acetate, 3:1) =0.08.

EXAMPLE 5

1,2-O-(3-pentylidene)-3,5,6-tri-O-sulfo-α-D-glucofuranose, tripotassium salt (Compound V)

A solution of 1,2-O-(3-pentylidene)-α-D-glucofuranose (6.8 g, 28 mmole) in dry pyridine (60 ml) was vigorously stirred and cooled to −30° C. A solution of chlorosulfonic acid (16 g, 138 mmole) in chloroform (35 ml) was added dropwise, while keeping the temperature of the reaction mixture between −30° C. and −15° C. After the addition was complete, the reaction mixture was allowed to gradually warm to ambient temperature over a 15–18 hour time period.

When analysis by TLC and paper electrophoresis indicated that sulfation was complete, the reaction mixture was cooled to −15° C. and treated according to the procedure outlined in Example 1.

After completing the ion exchange chromatography, the fractions containing the desired product were combined and neutralized to pH 7 by adding 1 M potassium hydroxide solution. The solvent was then removed under reduced pressure.

The product was recrystallized twice from a methanol/water mixture to yield 8.7 g (46 percent) of a white crystalline solid: TLC $R_f$=0.5; M (glucose-6-sulfate) =1.6; decomposition point 180° C.; $^1$H NMR (D$_2$O, chemical shifts relative to TMSPA) γ6.10 (d, 1H), 5.05 (d, 1H), 4.88 (d, 1H), 4.82–4.69 (m, 2H), 4.55–4.45 (m, 1H), 4.24–4.12 (m, 1H), 1.78 (q, 2H), 1.63 (q, 2H), 0.91 (t, 3H), 0.83 (t, 3H).

EXAMPLE 6

1,2-O-(5-Nonylidene)-α-D-glucofuranurono-α-6.3-lactone

A mixture of 2-mesitylenesulfonic acid (3.5 g, 14.8 mmole), 1,4-dioxane (360 ml), and triethyl orthoformate (46.8 g, 316 mmole) was cooled to zero degrees C. Freshly distilled 5-nonanone (351 g, 2.47 mole) was added dropwise. The reaction mixture was allowed to warm to ambient temperature and then stirred for an additional two hours.

Powdered D-glucofuranurono-6,3-lactone (35.0 g, 200 mmole) was added and the mixture was vigorously stirred until a clear solution was obtained (approximately 24 hours). The reaction mixture was then heated at 45° C. for 48 hours.

The resulting mixture was neutralized with triethylamine to a pH value of 7, filtered to remove unreacted starting material, and concentrated under reduced pressure. The resulting yellow-orange oil was diluted with chloroform and filtered to remove undissolved solids. The filtrate was washed with water, dried over anhydrous magnesium sulfate, filtered, and concentrated under reduced pressure.

The concentrated material crystallized on standing. The solid was broken up in hexane and collected by filtration to yield 18.5 g (31 percent) of a white crystalline solid: TLC $R_f$ (methylene chloride/methanol, 9:1, with a drop of acetic acid) 0.5; $^1$H NMR (CDCl$_3$, chemical shifts relative to TMS) $\gamma$6.03 (d, 1H), 5.02–4.89 (m, 1H), 4.87–4.72 (m, 2H), 4.65–4.42 (br s, 2H), 3.48–3.25 (br s, 1H), 1.80–1.64 (m, 2H), 1.61–1 50 (m, 2H), 1.45–1.33 (m, 8H), 1.08–0.81 (m, 6H).

EXAMPLE 7

1.2-O-(5-Nonylidene)-α-D-glucofuranose

A solution of 1,2-O-(5-nonylidene)-α-D-glucofuranurono-6,3-lactone (17.37 g, 58 mmole) in anhydrous THF (350 ml) was cooled to −70° C. with a dry ice/acetone bath. A 1.0 M solution of borane in THF (300 ml, 300 mmole) was then added dropwise while maintaining the temperature of the reaction mixture below −40° C.

The reaction mixture was allowed to stir for 48 hours at ambient temperature, then cooled to zero degrees C., and methanol (300 ml) was added dropwise. Upon warming to room temperature, the mixture was stirred for 2 hours and then concentrated under reduced pressure.

The product was recrystallized from THF/hexane to yield 12 g (69 percent) of a white solid: TLC $R_f$ (hexane/ethyl acetate, 1:1)=0.2; $^1$H NMR (D$_6$-DMSO, chemical shifts relative to TMS) $\gamma$5.84 (d, 1H), 5.00 (d, 1H), 4.61 (d, 1H), 4.41 (d, 1H), 4.22–4.18 (m, 2H), 4.01–3.96 (m, 1H), 3.92–3.79 (m, 1H), 3.76–3.76 (m, 1H), 3.56–3.47 (m, 1H), 1.68–1.57 (m, 6H).

EXAMPLE 8

1,2-O-(5-Nonylidene)-3,5,6-tri-O-sulfo-α-D-glucofuranose, tripotassium salt (Compound IV)

A solution of 1,2-O-(5-nonylidene)-α-D-glucofuranose (7.0 g, 23 mmole) in dry pyridine (90 ml) was vigorously stirred and cooled to -30° C. A solution of chlorosulfonic acid (9.8 g, 84 mmole) in chloroform (30 ml) was added dropwise while keeping the temperature of the reaction mixture between −30° C. and −15° C. After the addition was complete, the reaction mixture was allowed to gradually warm to ambient temperature over a 15–18 hour time period.

When analysis by TLC and paper electrophoresis indicated that sulfation was complete, the reaction mixture was cooled to −15° C., and treated according to the procedure outlined in Example 1, Recovery 1.

After completing the ion exchange chromatography, the fractions containing the desired product were combined and neutralized to pH 7 by adding 1 M potassium hydroxide solution. The solvent was then removed under reduced pressure.

The product was recrystallized twice from a methanol/water moisture to yield 11.5 g (75 percent) of a white crystalline solid: TLC $R_f$=0.5; M (glucose-6-sulfate) =1.4; decomposition point of 180° C.; $^1$H NMR (D$_2$O, chemical shifts relative to TMSPA) $\gamma$6.08 (d, 1H), 5.06 (d, 1H), 4.86 (d, 1H), 4.83–4.67 (m, 2H), 4.53–4.48 (m, 1H), 4.22–4.16 (m, 1H), 1.81–1.73 (m, 2H), 1.66–1.58 (m, 2H), 1.39–1.22 (m, 8H), 0.91–0.83 (m, 6H).

EXAMPLE 9

1,2-O-(Isopropylidene)-3,6-di-O-(diphenylphospho)-α-D-glucofuranose

A solution of 1,2-O-(isopropylidene)-α-D-glucofuranose (6.2 g, 28.2 mmole) in anhydrous pyridine (90 ml) was cooled to zero degrees C in an ice bath under a nitrogen atmosphere. Diphenyl chlorophosphate (25 g, 93.1 mmole) was added dropwise with vigorous stirring. After warming to ambient temperature, the reaction mixture was heated at 50° C. for 72 hours.

Upon completion of the reaction, H$_2$O (3 ml) was slowly added to the mixture. The reaction mixture was then filtered and concentrated under reduced pressure to leave a viscous brown oil.

The oil was taken up in ethyl acetate and this solution was washed sequentially with a 0.5 M hydrochloric acid solution, a saturated sodium bicarbonate solution, and water. The organic layer was dried over anhydrous sodium sulfate, filtered, and concentrated under reduced pressure.

The product was purified by column chromatography using silica gel 60 and a solvent system of methylene chloride: methanol (9:1, v/v). The fractions containing the desired product were combined and concentrated under reduced pressure to yield 5.6 g (38 percent) of an off-white solid: TLC $R_f$ (methylene chloride:methanol, 9:1)=0.3; $^1$H NMR (CDCl$_3$, chemical shifts relative to TMS) $\gamma$7.38–6.85 (m, 20H), 5.58 (d, 1), 5.28 (br s, 1H), 4.89–4.75 (m, 1H), 4.53–4.33 (m, 2H), 4.03–3.92 (m, 1H), 3.70–3.57 (m, 1H), 2.98 (br s, 1H), 1.36 (s, 3H), 1.19 (s, 3H).

EXAMPLE 10

1,2-O-(Isopropylidene)-3,6-di-O-phospho-α-D-glucofuranose, tetrapotassium salt (Compound VII)

To a solution of 1,2-O-(isopropylidene)-3,6-di-O-(diphenylphospho)-α-D-glucofuranose (1.4 g, 2.6 mmole) in ethanol (25 ml) were added 90 mg of platinum oxide. The suspension was shaken under 50 psi of hydrogen gas for 24 hours. The solution was then filtered through celite and the celite was rinsed with additional ethanol.

The filtrate was concentrated under reduced pressure, the residue was dissolved in water, and the solution was neutralized to pH 8 by adding a 1 M potassium hydroxide solution. This solution was concentrated under reduced pressure to yield 0.8 g (83 percent) of a white solid: TLC $R_f$=0.2; M )glucose-6-sulfate) =1.3; decomposition point 140° C.; $^1$H NMR (D$_2$O, chemical shifts relative to TMSPA) $\gamma$6.08 (d, 1H), 4.92–4.55 (m, 3H), 4.42–4.38 (m, 1H), 4.29–4.16 (m, 1H), 3.85–3.77 (m, 1H), 1.52 (s, 3H), 1.35 (s, 3H).

In the following examples, proton magnetic resonance (Pmr) spectra were recorded by means of a Nicolet 200 MHz spectrometer. Chemical shifts are reported in ppm downfield from internal tetramethysilane (TMS).

Reaction mixtures and products were routinely analyzed by high performance liquid chromatograph (HPLC) using a Bio-Rad Isocratic Model 1306 instrument with an ultraviolet (UV) detector set at a wavelength of 210 nm. The column used was a commercially available Lichrosorb Si-60 (5μ) normal phase silica gel column. The mobile phase was composed of acetonitrile, water, and ammonium hydroxide in the ratio by volume of 45:5:1, respectively.

Thin layer chromatographs (TLC) were developed on 10 cm glass slides coated with silica gel and a fluorescent indicator. Spots were visualized by charring after immersion in a 10 percent aqueous solution of sulfuric acid. The solvents used in developing TLC plates were: Solvent A - ethyl acetate; Solvent B - hexane/ethyl acetate (3:1).

Specific rotations were determined at 20° C. with a Rudolph Research Autopol II Polarimeter or at 23° C. with a Perkin-Elmer Model 241 Polarimeter.

EXAMPLE 11

1,2:5,6-Di-O-Cyclohexylidene-α-D-glucofuranose

To 758 g (7.7 moles) of cyclohexanone were added 260 g (1.44 moles) of anhydrous dextrose, followed by 20 ml of concentrated sulfuric acid. The mixture was heated to 35° C. and monitored by TLC. The flow rate of the desired product using Solvent A was $R_f=0.95$.

When the reaction was complete, the solution was cooled to 20° C. and carefully neutralized with excess potassium hydrogen carbonate to a pH of 9. The mixture was filtered and an equal volume of water was added. This mixture was concentrated under reduced pressure until a precipitate had begun to form. An equal volume of water was added and the mixture was extracted twice with ethylene dichloride. The combined organic extracts were washed twice with saturated aqueous sodium sulfate, filtered, and concentrated under reduced pressure to leave a heavy syrup. The syrup was diluted with hexane and allowed to cool slowly to 4° C. The crystalline product was filtered by suction filtration, washed with cold hexane, and dried under a vacuum at 40° C.

The melting point of the compound 1,2:5,6-di-O-cyclohexylidene-α-D-glucofuranose was 132° C.-124° C. The optical rotation of the compound was $[\alpha]_D^{20}$ (C2, EtOH)= −2.4°.

EXAMPLE 12

1,2:5,6-Di-O-cyclopentylidene-α-D-glucofuranose

To 70 g (0.389 mol) of anhydrous dextrose in 800 g (9.51 moles) of freshly distilled cyclopentanone were added 84 g (0.616 mol) of zinc chloride that had been freshly fused and pulverized. This mixture was stirred vigorously and 1.4 g (0.014 mol) of phosphoric acid (99 percent) were added. Stirring was continued and the mixture was heated to 40° C. for 48 hours.

After cooling to 25° C., the solids were removed by suction filtration and rinsed with ethylene dichloride. Solid sodium carbonate was added to the filtrate until a pH value greater than 7 was reached. This mixture was again subjected to suction filtration. The filtrate was diluted with an equal volume of ethylene dichloride and a 10 percent aqueous solution of sodium bicarbonate was added. The solids formed were removed by suction filtration and the organic layer was separated and extracted two additional times with 10 percent sodium bicarbonate solution. The organic extract was washed once with water, dried over anhydrous magnesium sulfate, filtered, and concentrated under reduced pressure to leave a viscous brown oil.

Upon distillation of the brown oil, 1,2:5,6-di-O-cyclopentylidene-α-D-glucofuranose distilled at 150° C.-170° C. as a light yellow viscous oil. With TLC analysis, the flow rate of this compound using Solvent B was $R_f=0.21$.

EXAMPLE 13

1.2:5.6-Di-O-butylidene-α-D-glucofuranose

To 36 g (200 mmol) of anhydrous dextrose were added 144 g (2.0 moles) of butyraldehyde. The mixture was stirred at 0° C. and 10 ml (120 mmol) of concentrated hydrochloric acid was added dropwise over a 15 minute period. The temperature of the reaction mixture rose to 43° C. and then dropped to 35° C. where it was maintained by means of a heating mantle for 3 hours.

After stirring about 15-18 hours at 25° C., the reaction mixture was neutralized with saturated sodium bicarbonate solution and extracted twice with toluene. The combined organic extracts were dried over anhydrous magnesium sulfate, filtered, and concentrated under reduced pressure to leave a light yellow viscous oil.

This residue was purified by high vacuum distillation and 1,2:5,6-di-O-butylidene-α-D-glucofuranose was obtained as the fraction boiling at 170° C.-210° C. (0.15 mm Hg). Analysis of the distillate indicated that the desired product was obtained as a mixture of isomers in a total purity greater than 97 percent. Pmr (CDCl$_3$) γ6.00-5.82 (m, 1H), 5.45-4.84 (m, 4H), 4.72-2.95 (m, 5H), 1.83-1.22 (m, 8H), 1.18-0.78 (m, 6H).

EXAMPLE 14

1,2:5,6-Di-O-(4-heptylidene)-α-D-glucofuranose

To 510 g (4.47 moles) of 4-heptanone were added 40 g (255 mmol) of anhydrous dextrose. The mixture was stirred and 55 g (403 mmol) of freshly fused and pulverized zinc chloride and 0.92 g (9.3 mmol) of phosphoric acid (99 percent) were added. Stirring was continued and the mixture was heated to 40° C. for 48 hours.

After cooling to 25° C., the reaction mixture was treated as discussed in Example 12.

With TLC analysis, the flow ate of 1,2:5,6-di-O-(4-heptylidene)-α-D-glucofuranose using Solvent B was $R_f=0.28$.

A compound of the invention is prepared by suitable reaction of a compound prepared in Examples 11-14 as discussed elsewhere herein.

EXAMPLE 15

Inhibition of Gastric Ulcers Induced by Ethanol Alone and by Ethanol with Heparin In the presence of stress, heparin has been found to provoke a delayed and significant tendency to cause bleeding from vulnerable organs, due to an adverse effect on vascular endothelium, long after its anticoagulant action has dissipated (Jaques, *Chest*, 88:751, 1985).

This non-anticoagulant action of heparin has been used to develop a method that provokes the bleeding ulcer phenomenon, so that its possible control by a drug can be studied. In this method, a relatively large amount of ethanol is administered to rats by oral gavage (1.0 ml/200 gm), a procedure widely used to produce ordinary gastric ulceration. This injection, however, is given in combination with the intraperitoneal injection of heparin sulfate (10 mg/kg). Ethanol or heparin, when administered alone, as above, do not produce gastric hemorrhage. Given together they do, after 17 and before 24 hours following their combined administration. This phenomenon has nothing to do with failed blood coagulation, since coagulation time becomes normal by six hours after heparin injection.

Compound III inhibits both the ulcer and the bleeding phenomena. The results of a typical study are shown below where group numbers of animals studied (n) was between 9 and 13. Compound III treatment was 50 mg/kg by oral gavage in distilled water as diluent, at 45 minutes before ulcer induction.

The effects of ethanol alone and ethanol plus Compound III were assessed four hours after ethanol administration. The effects of ethanol plus heparin and ethanol plus heparin plus Compound III were assessed 24 hours after administration of the ulcer inducing combination. Ulcer formation was assessed as discussed in Example 16.

In this and the following examples, the potassium salt of the drug indicated by a Roman numeral was used; i.e., M is potassium ($K^+$).

|   | Groups | Frequency of Ulcer-Bearing Rats, as Percent of Total in Group | |
|---|---|---|---|
|   |   | A Ulcers | B Bleeding Ulcers |
| A. | Ethanol Only | 56 | 0 |
|   | Ethanol + Compound III | 11 | 0 |
| B. | Ethanol + Heparin | 85 | 62 |
|   | Ethanol + Heparin + Compound III | 25 | 0 |

Chi square analysis: Compound III inhibits the formation of ulcers without regard to type; when control (ulcer-induced) and drug-treated groups from Sections A and B are combined, $P<0.01$.

Compound III inhibits bleeding ulcer formation, $P<0.01$.

EXAMPLE 16

Development of Gastric Pathology Following Inflammatory Stress and Indomethacin: its Suppression by Compound III Stress was induced by the following procedure. On day one, under ether anesthesia, 18 male Sprague Dawley rats were injected with a suspension of Zymosan A (1 mg/ml in normal saline; Sigma Chemical Co.) in each hind paw. Swelling developed and persisted. This treatment generated activated blood complement locally (including the C5a moiety), which then spread by the bloodstream throughout the animal. In the hind feet, the treatment induced local persistent inflammation and discomfort, and contributed to the development of gastric pathology at a distance.

Twenty-four hours later all rat paws were reinjected, this time with 0.1 ml of proinflammatory zymosan-activated rat serum containing additional amounts of inflammatory complement fragment C5a (as in Example 19, hereinafter). Five hours later 30 mg/kg indomethacin in an aqueous suspension was given to nine such rats by oral gavage. These rats also received a subcutaneous injection of 0.1 ml normal saline. Nine other such rats were given indomethacin as above, and Compound III (50 mg/kg in normal saline subcutaneously). Four additional rats, not stressed (normal) were given water by gavage as a placebo and saline subcutaneously. All rats were fed ad libitum on standard diet.

Twenty-four hours later all animals were sacrificed by ether euthanasia. Their stomachs were washed with saline and evaluated for ulcer-related pathology using an illuminated magnifying glass. This assay is similar to that reported by Kinney et al., *J. Med. Chem.*, 33:327 (1990). Separately, the stress and indomethacin induced no ulceration.

Results

Rat Stomachs - Normal

1) Supple; endothelium is satin-smooth, pink.
2) Supple; endothelium is satin-smooth, pink.
3) Supple; endothelium is satin-smooth, pink.
4) Supple; endothelium is satin-smooth, pink.

Rat Stomachs - Stress +Indomethacin

1) Relatively rigid and ridged; endothelium is dry, gritty and pale yellow. No ulceration. Pathology score: ½.

2) Appearance as #1; one circular ulcer. Pathology score: 1.0.

3) Appearance as normal stomach. No ulceration. Pathology score: 0.0.

4) Appearance as normal stomach. No ulceration. Pathology score: 0.0.

5) Appearance as #1; one ulcer with clotted blood in and adjacent to opening in mucosa. Pathology score: 4.0.

6) Appearance as #1; one perforated ulcer, ringed with clotted blood. Pathology score: 7.0.

7) Appearance as #1; no ulceration. Pathology score: ½.

8) Appearance as #1; no ulceration. Pathology score: ½.

9) Appearance as #1; no ulceration. Pathology score: ½.

Mean Pathology score: 1.43

Rat Stomachs - Stress +Indomethacin +Compound III

1) Supple; endothelium is satin-smooth, pink. Pathology score: 0.0.
2) Supple; endothelium is satin-smooth, pink. Pathology score: 0.0.
3) Supple; endothelium is satin-smooth, pink. Pathology score: 0.0.
4) Supple; endothelium is satin-smooth, pink. Pathology score: 0.0.
5) Supple; endothelium is satin-smooth, pink. Pathology score: 0.0.
6) Supple; endothelium is satin-smooth, pink. Pathology score: 0.0.
7) Supple; endothelium is satin-smooth, pink. Pathology score: 0.0.
8) Supple; endothelium is satin-smooth, pink. Pathology score: 0.0.
9) Supple; endothelium is satin-smooth, pink. Pathology score: 0.0.

Mean Pathology score: 0.00

It is seen that use of a compound of this invention can inhibit ulceration and pre-ulcerative stomach pathology caused by stress and indomethacin. Thus, indomethacin can be more safely administered for its usual anti-inflammatory and pain killing effects when co-administered with a compound of this invention.

EXAMPLE 17

Development of Gastric Pathology Following Inflammatory Stress and Indomethacin: its Suppression by Compound III In contrast to the study of Example 16, above, in this study animals were food deprived for 24 hours before and also during the 24 hours following drug treatments. All animals were subjected to the inflammatory stress as described in Example 16. Eight such rats received 30 mg/kg indomethacin, and eight rats received indomethacin and Compound III (subcut., 50 mg/kg). Four rats, not stressed, were given placebo by gavage.

All animals were sacrificed by ether euthanasia 24 hours later, and their stomachs evaluated for ulcer-related pathology.

Results

In the stressed animals given indomethacin alone, pathology was much more severe than in Example 16. For scoring, therefore, the frequency of ulcers per rat stomach was quantified, and whether they were or were not bleeding.

In the group given indomethacin alone, all eight rats had 1–5 ulcers. Of a total of 23 ulcers found in this group, 22 were bleeding. In the group given indomethacin and also treated with Compound III, only two rats had two and three ulcers, respectively. None were bleeding.

| | Per Rat | |
|---|---|---|
| Group | Total Ulcer Frequency Mn ± SE | Bleeding Ulcer Frequency Mn ± SE |
| Indomethacin | 2.88 ± 0.67 | 2.65 ± 0.063 |
| Indomethacin + Compound III | 0.63 ± 0.42 | 0.00 |

This study again illustrates the ulcer-producing effect of indomethacin and the striking capacity of a compound of this invention to suppress this undesirable side effect of indomethacin when administered along therewith.

EXAMPLE 18

Inhibition of the Injury of Organ Ischemia (Depressed Organ Blood Flow, Producing Oxygen Lack)

This important disease model is used to evaluate aspects of tissue injury that occur in heart attack, or myocardial infarction, and stroke. Under these conditions, a significant period of injury can occur after blood flow has been restored, during the period of reperfusion. In this period, injury results from attack by superoxide and related redox-active compounds and free radicals. To evaluate the effect of drugs of the invention on damaging events in this period, ischemia of the rat paw was induced according to the method of Oyanagui, *Free Radical Research Communications.* 4:385, (1988), and was treated as discussed below.

To produce ischemia, blood flow to the left hind foot was largely interrupted by application of a tourniquet made up of two size 18 rubber bands wound eight times around the leg just behind the heel. This tourniquet was left in place for 45 minutes and then removed. Both application and removal of tourniquet were carried out under ether anesthesia. Injury was equated with organ swelling, which was assayed by measurement of the dorsoventral foot diameter with a Schnelltaster caliper, just before application of the tourniquet and at various times following tourniquet removal, during the reperfusion period.

Rats employed were Sprague Dawley males, weighing 240–280 grams. Drug comparisons were made here employing measurements 30 minutes into the reperfusion period. The widely studied drug allopurinol, a xanthine oxidase inhibitor and a free radical scavenging agent, used in the treatment of gout, and widely used to suppress experimental post-ischemic reperfusion injury was used as an experimental treatment standard. In studies below, allopurinol and all new drugs were given intraperitoneally just prior to application of tourniquet. Data are reported as the mean swelling (Mn) ±standard error (SE). The control for each group was the observed swelling without drug treatment, whereas the indicated drug treatment data were obtained by causing the ischemia plus treatment with the indicated drug. Group n is 5 or 6.

| | Post-Ischemic Reperfusion 30 Minute Paw Swelling (0.1 mm, Mn ± SE) | Swelling Change as a Result of Treatment |
|---|---|---|
| A. Control | 12.7 ± 0.98 | |
| Compound III (0.2 mg/kg) | 6.0 ± 0.32 | −53% |
| B. Control | 20.5 ± 0.76 | |
| Compound III (0.2 mg/kg) | 12.2 ± 0.70 | −40% |
| Allopurinol (20 mg/kg) | 13.3 ± 0.56 | −35% |
| C. Control | 18.4 ± 0.54 | |
| Compound III (0.2 mg/kg) | 10.2 ± 0.28 | −45% |
| Compound VI (0.2 mg/kg) | 9.1 ± 0.27 | −50% |
| D. Control | 11.4 ± 0.51 | |
| Compound IV (0.2 mg/kg) | 21.2 ± 2.25 | +86%* |

*edema enhancement

All of the above drug effects are significant by Student's t test at levels of $P < 0.02$.

EXAMPLE 19

Injury Provoked by Zymosan-Activated Serum: Its Relation to Polymorphonuclear Cell Accumulation Zymosan is a complex yeast cell wall polysaccharide that activates blood complement by the indirect route, generating inflammatory polypeptides such as C5A, a so-called "bugle call" protein, that is highly chemotactic for neutrophils. The contributing and causative role for neutrophils in the development of stroke and in the pathology that occurs in the reperfusion period following clot-lysis in myocardial infarction has been the subject of intensive research for the last several years, Lucchesi, *Ann. Rev. Physiol.*, 51:561, (1980).

For the present studies, zymosan-activated serum (ZAS) was made by incubating reconstituted lyophilized rat serum with 10 mg/ml zymosan A for one hour at 37° C., and then microfiltering to remove the zymosan.

In the first study, 0.1 ml ZAS and 0.1 ml normal serum (NS) were injected into opposite hind paws of the same rat under either anesthesia. Distilled water vehicle or 50 mg/kg Compound III in water were given by gavage to 9 control and 9 drug-treated adult male rats, respectively, and 90 minutes later the dorsoventral diameter of the hind feet were determined by Schnell-taster caliper. Sera were thereafter injected into rat hind paw footpads as described. Below are given the paw swellings that developed at 2 and 3 hours, in response to ZAS and to normal serum, in the absence and presence of drug treatment. Data are reported as in the prior example.

| Hour post- | Paw Swelling (0.1 mm) | | Swelling Change |
|---|---|---|---|
| | ZAS | ZAS + Compound III | |
| 2 | 27.22 ± 1.97 | 10.78 ± 1.94 | −60% |
| 3 | 28.89 ± 2.48 | 16.11 ± 2.94 | −44% |
| | NS | NS + Compound III | |
| 2 | 11.22 ± 1.28 | 7.67 ± 1.41 | −32% |
| 3 | 11.44 ± 1.55 | 9.44 ± 1.28 | −17% |

By Student's t test, drug inhibition of ZAS-induced inflammation is significant at levels of $P<0.01$.

The relationship of neutrophil infiltration to ZAS-induced swelling, and its drug-inhibition, was evaluated in another study. In this study, all procedures employing ZAS and Compound III were carried out as above, except that, also, standardized samples of the swollen footpads were removed and subjected to analysis for myeloperoxidase activity (MPO), according to the method of Lundberg et al., *Inflammation*, 7:247, (1983). MPO is a neutrophil-specific enzyme, and its assay is the most widely used method of identifying the degree of neutrophil participation in organ pathology.

| Group | Paw Swelling (0.1 mm) | MPO (Rel. Units) |
|---|---|---|
| Normal (Untreated) (n = 6) | — | 11.67 ± 1.87 |
| ZAS alone (n = 12) | 34.58 ± 2.45 | 94.42 ± 12.81 |
| ZAS + Compound III (17 mg/kg) (n = 6) | 16.83 ± 2.12 | 32.17 ± 2.83 |
| ZAS + Compound III (50 mg/kg) (n = 12) | 15.25 ± 3.99 | 41.67 ± 8.93 |

Drug inhibitions of paw swelling and MPO accumulation are highly significant by Student's t test, all at levels of $P<0.01$.

EXAMPLE 20

In Vitro Neutrophil Chemotaxis

In vitro neutrophil chemotaxis studies were carried out by standard methods, as follows:

Mice were injected with complete Freund's adjuvant (CFA) and peritoneal cells, principally neutrophils (>90 percent), were removed from the mice 24 hours thereafter. Blind-well chemotactic chambers (Nucleopore Corp., Pleasanton, California) were utilized.

Medium (RPMI 1640 plus 10 percent fetal calf serum) or medium plus 20 percent zymosan-activated rat serum (ZAS) was added to the lower compartment of each chamber. A nucleopore filter (8μm pore size) was placed between compartments and $1 \times 10^5$ peritoneal neutrophils (above) suspended in medium were placed in the upper compartment. Chambers were incubated for six hours, after which time the filters were removed and stained with Giemsa stain. The number of cells on the lower surface of the filter was counted under a microscope. Treatment groups were assayed in duplicate.

The studies were carried out more specifically as follows:

Zymosan (Sigma Chemical Co., St. Louis, Mo.) was mixed with rat serum for one hour at 37° C. at 1 milligram (mg)/ml. The resulting chemoattractant composition was filtered, aliquotted and stored frozen at −70° C. prior to use.

The above chemoattractant composition was used as a 20 percent v/v solution in medium.

The chemotaxis chambers were arranged as follows:

| Chamber # | Bottom | Top |
|---|---|---|
| 1–2 | medium | cells (0.1 ml) + medium (0.1 ml) |
| 3–4 | chemoattractant | cells (0.1 ml) + medium (0.1 m.) |
| 5–6 | chemoattractant | cells (0.1 ml) + drug (0.1 ml) |
| 7–8 | chemoattractant | cells (0.1 m.) + drug (0.1 ml) |

The chambers were incubated at 37° C. for six hours, after which the chambers were dismantled, and the filters removed and treated as follows:

a) The filters were immersed in Giemsa stain diluted 1:50 for 30–45 minutes.
b) The stained filters were rinsed gently in distilled water for 3–5 minutes.
c) The stained, rinsed filters were air dried without blotting.

Several compounds described herein and control compounds ("drug", above) were examined at various concentrations. The molar concentration of a drug that inhibited the observed chemotaxis by 50 percent, defined as the ID 50 value, was determined as shown below.

| Drug | $ID_{50}$ (M) |
|---|---|
| Compound II | $3 \times 10^{-5}$ |
| Compound III | $2 \times 10^{-7}$ |
| Compound IV | $>1 \times 10^{-5}$ |
| Compound V | $2 \times 10^{-6}$ |
| Compound VI | $1 \times 10^{-6}$ |
| Compound VII | $>1 \times 10^{-4}$ |
| Probenecid | $3 \times 10^{-6}$ |
| SITS* | $>2 \times 10^{-5}$ |
| Ibuprofen | $>5 \times 10^{-5}$ |
| Prednisone | $>>5 \times 10^{-5}$ |
| $PGE_2$** | $1 \times 10^{-7}$ |

*SITS = 4-Acetamido-4'-isotheiocyano-stilbene-2,2'disulfonate
**$PGE_2$ = Prostaglandin $E_2$ Data from nine separate studies are shown below.

| Study Number | Drug | Dose (μg/ml) | Percent Inhibition |
|---|---|---|---|
| I | Compound III | 100.0 | 68.0 |
| | | 200.0 | 60.0 |
| II | Compound III | 0.1 | 55.0 |
| | | 1.0 | 69.0 |
| | | 10.0 | 87.0 |
| | | 100.0 | 80.5 |

-continued

| Study Number | Drug | Dose (μg/ml) | Percent Inhibition |
|---|---|---|---|
| III | Compound III | 0.1 | 47.0 |
| | | 1.0 | 65.0 |
| | | 10.0 | 76.0 |
| | Compound IV | 0.1 | 24.0 |
| | | 1.0 | 44.0 |
| | | 10.0 | −26.5 |
| | Compound VI | 0.1 | 21.0 |
| | | 1.0 | 44.0 |
| | | 10.0 | 85.0 |
| IV | Compound III | 0.1 | 68.5 |
| | | 1.0 | 90.0 |
| | | 10.0 | 92.5 |
| | Compound IV | 0.1 | 4.5 |
| | | 1.0 | 28.5 |
| | | 10.0 | −52.5 |
| | Compound VI | 0.1 | −12.0 |
| | | 1.0 | 47.0 |
| | | 10.0 | 85.0 |
| V | Compound III | 0.1 | 70.0 |
| | | 1.0 | 88.5 |
| | | 10.0 | 97.5 |
| | Compound V | 0.1 | −8.0 |
| | | 1.0 | 62.0 |
| | | 10.0 | 101.0 |
| | Probenecid | 0.1 | 5.5 |
| | | 1.0 | 59.5 |
| | | 10.0 | 89.5 |
| VI | Compound III | 0.1 | 77.0 |
| | Compound VII | 0.1 | 8.0 |
| | | 1.0 | 23.0 |
| | | 10.0 | 29.0 |
| | Compound II | 0.1 | 2.5 |
| | | 1.0 | 45.5 |
| | | 10.0 | 48.5 |
| | SITS | 0.1 | 18.5 |
| | | 1.0 | −12.5 |
| | | 10.0 | 48.5 |
| VII | Compound III | 0.1 | 47.5 |
| | | 1.0 | 77.0 |
| | | 10.0 | 87.0 |
| | Ibuprofen | 0.1 | 17.5 |
| | | 1.0 | 9.3 |
| | | 10.0 | 35.5 |
| | Prednisone | 0.1 | 15.5 |
| | | 1.0 | 16.0 |
| | | 10.0 | 20.0 |
| VIII | Compound III | 0.01 | 1.5 |
| | | 0.1 | 38.0 |
| | | 1.0 | 63.5 |
| | | 10.0 | 74.5 |
| | PGE$_2$ | 0.2 | 71.5 |
| IX | Compound III | 0.1 | 43.0 |
| | | 1.0 | 70.0 |
| | PGE$_2$ | 0.01 | 71.0 |
| | | 0.1 | 91.5 |
| | PGE$_2$(0.1) + Compound III | 0.1 | 73.5 |
| | | 1.0 | 77.5 |
| | PGE$_2$(0.1) + Compound III | 0.1 | 93.5 |
| | | 1.0 | 85.0 |

The above data are uncorrected for the average small degree of non-attractant-induced cell migration.

The above data illustrate that at about 10 μg/ml, attractant-induced chemotaxis fell in the range of about 75–90 percent for Compound II. That compound was also about 2–3 orders of magnitude (about 100–1000) times as potent as ibuprofen and prednisone.

By microscopic examination, Compound VI was observed to exhibit a diffuse toxic granularity in the cells. By similar study, probenecid treatment caused a stringy, elongated deformation in the neutrophils. The above were the only expressions of cytotoxicity observed to affect the neutrophils in this study.

EXAMPLE 21

Inflammation Provoked by Carrageenan Infection

Carrageenan is a complex sulfated polysaccharide derived from Irish moss. It is the most classic acute inflammation inducer used in pharmacology, and anti-inflammatory effects of aspirin-like drugs against carrageenan edema in laboratory animals are predictive of their order of potency in arthritis in man.

In this study employing mice, anti-inflammatory effects of Compound III were compared to those of the free radical-inhibiting enzyme superoxide dismutase (SOD). Treatments were given intravenously, 45 minutes after injection of 150 μg carrageenan (in saline) per foot pad. To assess swelling, foot pad dorsoventral diameters were measured at zero time and two hours after carrageenan injection.

| | Foot-Pad Swelling (0.1 mm) | Swelling Change |
|---|---|---|
| Control (n = 8) | 3.8 ± 0.67 | |
| SOD (100 units) (n = 8) | 1.55 ± 0.31 | −51% |
| Compound III (50 mg/kg) (n = 8) | 0.82 ± 0.46 | −74% |

Effects of both treatments are significant by Student's t test at levels of $P < 0.01$.

EXAMPLE 22

Development of Gastric Ulcers in Rats with Corona Virus Infection, and Treated with Indomethacin: its Suppression by Compound III and the Anti-Ulcer Drug Cimetidine Corona virus is a non-lethal upper respiratory viral pathogen that not infrequently infects rat colonies. It is a type of rodent coryza or catarrh, the equivalent of a disease that falls somewhere between human influenza and a severe common cold. The animals of this experiment suffered from this condition, a circumstance which was evident by observation, and which was confirmed by virological diagnosis at the Biological Resources Laboratory of the University of Illinois at Chicago. Since stress is a common component of peptic ulcer development in both animals and man, it was concluded that this feature of the status of these experimental animals rendered them appropriate for an ulcer study.

In this study, animals were not food deprived and were divided into treatment groups such that 15 rats received 30 mg/kg indomethacin alone (by oral gavage), 14 rats received indomethacin plus an injection of 25 mg/kg cimetidine subcutaneously, and 7 rats received indomethacin plus subcutaneous injection of 17.5 mg/kg of Compound III.

All animals were sacrificed by ether euthanasia 24 hours later and their stomachs evaluated for ulcer pathology. In this study ulcers were not hemorrhagic. Results are shown below as the average number of stomach ulcers per stomach.

| Treatment Group | Per Stomach Ulcer Frequency Mn ± SE |
|---|---|
| Indomethacin | 2.53 ± 0.52 |
| Indomethacin + cimetidine | 1.07 ± 0.25 |
| Indomethacin + Compound III | 0.86 ± 0.46 |

The above results show that the average ulcer frequency is about 2.5 ulcers/per rat in the control group. Cimetidine in the dose given reduces this frequency by 58 percent, whereas Compound III, in the dose given reduces ulcer frequency by 66 percent. Both drug effects are statistically significant, at $P<0.02$.

EXAMPLE 23

Effect on Established Adjuvant Arthritis

Adjuvant arthritis was studied because it allows gaining of insight into effects of a drug in established and chronic inflammatory disease. Adjuvant arthritis shares certain features with rheumatoid arthritis but it is distinct. It is widely used in industry because it allows one to predict the potency of non-steroidal anti-inflammatory drugs (NSAID's) [Weichman, in *Pharmaceutical Methods in the Control of Inflammation*, Chang et al., eds.; Alan R. Liss, New York (1989) p.362].

The rats used were of the Lewis strain, especially vulnerable to disease induction. Chronic polyarthritis was induced by the subcutaneous injection of complete Freund's adjuvant (CFA) into the rat tail. The CFA employed consists of 10 mg/ml heat-killed tubercle bacilli suspended in paraffin oil. An amount of 0.1 ml is injected, and the disease is allowed to develop over 14 days before daily assessments are made and treatments are initiated. Measurements that assess both increase in hind paw joint swelling and loss in hind limb function are taken.

Indomethacin was employed as a reference standard. Treatment effects of Compound III, alone and in combination with indomethacin were assessed. Compound III was dissolved in water and indomethacin was suspended in water by homogenization. Both were administered sequentially by oral gavage.

Measurements by caliper include the lateral diameter of the ankle joint of each hind limb, and the dorsoventral diameter of the foot, just behind the toes. The prime measurement of function focuses on the fact that in many animals by day 14, and in most animals by day 16 after adjuvant administration, the arthritic rat can lose use of his hind limbs, which then are dragged behind him like logs. To quantify the recovery of function during treatment, a technique of Martel et al., *Agents Actions*, 15:403 (1984) was adapted. A blind assessment of the number of animals in each group that were able to draw their leg(s) under them and have these bear weight was carried out.

A large study employing this screen is currently underway. In an initial treatment study lasting only four days; i.e., through 18 days after CFA administration, a highly significant enhancement of the rate of restoration of hind limb function was produced by orally administered Compound III when given together with indomethacin. Determination of difference in end point of functional change will require greater numbers, and is being determined.

EXAMPLE 24

Generalized Schwartzmann Reaction in the Rabbit

The Generalized Schwartzmann Reaction (GSR) is a pathology in which two intravenous injections of non-lethal amounts of bacterial endotoxin, when separated by 8 to 36 hours, produce intravascular coagulation, kidney cortical necrosis and hemorrhage, and pulmonary edema and hemorrhages, in otherwise untreated rabbits. The pathology in question has been found to be in large part a consequence of the behavior of activated neutrophils [Niemetz et al., *Nature London New Biol.*, 232:247 (1971)].

In this study, 100 µg of *E. coli* endotoxin was administered IV, 45 minutes after drug or placebo administration by oral gavage, on day one and on day two, twenty hours later. Animals were sacrificed for organ evaluation 48 hours after the second endotoxin injection. Eight animals per group (n=8) were evaluated.

Gross pulmonary hemostasis and hemorrhage were present in all control endotoxin-treated animals. Frank lung surface ulceration was present in five of the control endotoxin-treated animals. Administration of 50 mg/kg of Compound III in water by oral gavage given five minutes before each endotoxin injection suppressed these pathologic stigmata in the lung.

EXAMPLE 25

Acute Toxicology in the Mouse

Acute intraperitoneal and oral toxicity of Compound III was studied in the mouse. Ten animals per dose were employed.

The intraperitoneal $LD_{50}$ of Compound III in normal saline was 2.8 g/kg. However, 3.0 g/kg gave no toxicity by the intravenous route. Nor was oral death produced by the highest dose employed, 4.5 g/kg, in water.

EXAMPLE 26

Effect on Bleeding Time

The effect of an exemplary compound of the invention, Compound III, on bleeding time was also assessed as compared with aspirin. Bleeding was induced by a standardized transection of mouse tail tips, and subsequent bleeding time was determined after vertical immersion of the tails in isotonic saline at 37° C. for 30 seconds. Orally administered Compound III was found to be about equipotent with aspirin in prolonging mouse tail bleeding.

This assay is widely used and is known to reflect the degree of intravascular platelet aggregation. The assay is one used to evaluate the suppression of platelet aggregation by drugs. It is noted that the tendency of platelets to aggregate can contribute to the development or extension of clots and thus induce or worsen stroke or myocardial infarction.

EXAMPLE 27

Blood Coagulation Study

Heparin and dextran sulfate are noted for their activity in inhibiting blood coagulation. To assess the effect on coagulation, if any, of a compound of the invention, a comparative evaluation was made using mouse blood.

Heparin at 10 µg/ml in normal saline, Compound III at 10 µg/ml in normal saline and normal saline were placed in separate tubes. One ml of freshly drawn mouse blood was added to each tube, and the tube contents were mixed. The clotting time was then noted for each tube, and the results are as shown below:

| Assay Group | Mouse No. | Clotting time (minutes) | Average clotting time |
|---|---|---|---|
| Control | 1 | 5.0 | 4.33 ± 1.20 |
|  | 2 | 2.0 |  |
|  | 3 | 6.0 |  |
| Heparin | 1 | >60 | >60 |
|  | 2 | >60 |  |
|  | 3 | >60 |  |
| Compound III | 1 | 2.0 | 2.0 ± 0.71 |
|  | 2 | 1.0 |  |
|  | 3 | 4.0 |  |
|  | 4 | 1.0 |  |

As can be seen from the above data, heparin had a profound effect upon the coagulation time by making the blood uncoagulatable after 60 minutes, whereas a compound of the invention did not prolong the coagulation time.

The foregoing is intended as illustrative of the present invention but not limiting. Numerous variations and modifications may be effected without departing from the true spirit and scope of the novel concepts of the invention.

What is claimed is:

1. A glucofuranose substituted at the 3,5,6- or 3,6-positions by a sulfate, phosphate, or carboxylate radical that is anionic at a pH value of 7.2–7.4, the anionic charge of said radical being neutralized by a proton, an alkali metal ion or an ammonium ion.

2. The glucofuranose of claim 1 wherein the 1- and 2-position oxygen atoms are etherified, with the non-glucofuranose portion of the ether groups containing a total of up to 9 carbon atoms.

3. The glucofuranose of claim 2 wherein the ether is an acetal or ketal.

4. A compound having a structural formula

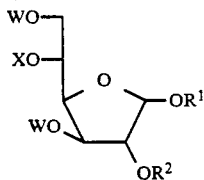

wherein W is selected from the group consisting of $SO_3M$, $PO_3M_2$ and $R^5CO_2M$ in which $R^5$ is $(CH_2)_n$, where n is 1–5;
X is H or W;
$R^1$ is H or $C_1$–$C_6$ alkyl;
$R^2$ is H or $C_1$–$C_6$ alkyl; or
$R^1$ and $R^2$ together form a $CR^3R^4$ group in which (a) $R^3$ and $R^4$ are independently selected from H or $C_1$–$C_6$ alkyl with the total number of carbon atoms in $CR^3R^4$ being nine or less, or (b) $CR^3R^4$ together form an unsubstituted cycloaliphatic group containing a total of 5–9 carbon atoms in the ring; and M is selected from the group consisting of a proton, an alkali metal ion, and ammonium ion.

5. The compound of claim 4 is $SO_3M$ and X is W.

6. The compound of claim 5 wherein $R^1$ and $R^2$ together form a $CR^3R^4$ group.

7. The compound of claim 6 wherein said $CR^3R^4$ group is selected from the group consisting of 2-propylidene, 3-pentylidene and 5-nonylidene.

8. The compound of claim 4 wherein W is $PO_3M_2$ and X is H.

9. The compound of claim 8 wherein $R^1$ and $R^2$ together form a $CR^3R^4$ group.

10. 1,2-O-(2-Propylidene)-3,5,6-tri-O-sulfo-D-glucofuranose, tripotoassium salt.

11. 1,2-O-(3-Pentylidene)-3,5,6-tri-O-sulfo-D-glucofuranose, tripotassium salt.

12. 1,2-O-(5-Nonylidene)-3,5,6-tri-O-sulfo-D-glucofuranose, tripotassium salt.

13. 3,5,6-tri-O-sulfo-D-glucofuranose, tripotassium salt.

14. 1,2-O-(2-propylidene)-3,6-di-O-phospho-D-glucofuranose, tetrapotassium salt.

15. A method of treating an inflammatory or ulcerative condition in a mammal comprising administering to a mammal an anti-inflammatory effective amount of a glucofuranose substituted at the 3,5,6- or 3,6-positions by a sulfate, phosphate or carboxylate radical that is anionic at a pH value of 7.2–7.4, the anionic charge of said radical being neutralized by a proton, alkali metal ion or an ammonium ion.

16. The method of claim 15 wherein the 1- and 2-position oxygen atoms of the substituted glucofuranose are etherified as a ketal or acetal containing a total of up to 9 carbon atoms.

17. The method of claim 16 wherein said glucofuranose contains sulfo groups at the 3,5,6-positions.

18. The method of claim 16 wherein said glucofuranose contains phosphono groups at the 3,6-positions.

19. The method of claim 15 wherein said inflammatory condition is edema.

20. The method of claim 15 wherein said inflammatory condition is gastric ulceration.

21. The method of claim 15 wherein said inflammatory condition is ischemia-induced.

22. A pharmaceutical composition comprising a physiological tolerable diluent and an anti-inflammatory effective amount of a glucofuranose substituted at the 3,5,6- or 3,6-positions by a sulfate, phosphate or carboxylate radical that is anionic at a pH value of 7.2–7.4, the anionic charge of said radical being neutralized by a proton, alkali metal ion or an ammonium ion.

23. The pharmaceutical composition of claim 22 wherein the 1- and 2-position oxygen atoms of the substituted glucofuranose are etherified as a ketal or acetal containing a total of up to 9 carbon atoms.

24. The pharmaceutical composition of claim 22 wherein said glucofuranose contains sulfo groups at the 3,5,6-positions.

25. The pharmaceutical composition of claim 22 wherein said glucofuranose contains phosphono groups at the 3,6-positions.

* * * * *